(12) United States Patent
Alem

(10) Patent No.: US 10,656,079 B2
(45) Date of Patent: May 19, 2020

(54) UV SOLID STATE DETECTION AND METHODS THEREFOR

(71) Applicant: Micro Detect, Inc., Tustin, CA (US)

(72) Inventor: Mehdi Alem, Tustin, CA (US)

(73) Assignee: MICRO DETECT, INC., Tustin, CA (US)

( * ) Notice: Subject to any disclaimer, the term of this patent is extended or adjusted under 35 U.S.C. 154(b) by 0 days.

(21) Appl. No.: 15/559,026

(22) PCT Filed: Jan. 24, 2017

(86) PCT No.: PCT/US2017/014732
§ 371 (c)(1),
(2) Date: Sep. 15, 2017

(87) PCT Pub. No.: WO2017/136187
PCT Pub. Date: Aug. 10, 2017

(65) Prior Publication Data
US 2019/0003962 A1 Jan. 3, 2019

Related U.S. Application Data

(60) Provisional application No. 62/388,545, filed on Feb. 1, 2016.

(51) Int. Cl.
*G01N 21/33* (2006.01)
*G01N 21/71* (2006.01)
*G01N 21/65* (2006.01)
*G01N 33/68* (2006.01)

(52) U.S. Cl.
CPC ............ *G01N 21/33* (2013.01); *G01N 21/65* (2013.01); *G01N 21/718* (2013.01); *G01N 33/6845* (2013.01)

(58) Field of Classification Search
CPC combination set(s) only.
See application file for complete search history.

(56) References Cited

U.S. PATENT DOCUMENTS

| | | | |
|---|---|---|---|
| 6,436,649 B1 | 8/2002 | Kohl et al. | |
| 8,617,827 B2 | 12/2013 | Hell et al. | |
| 2002/0007687 A1* | 1/2002 | Zimmermann | G01N 1/02 73/864.71 |
| 2003/0059855 A1* | 3/2003 | Cunningham | B01L 3/5085 435/7.9 |
| 2003/0211454 A1* | 11/2003 | Thomas | C09B 23/08 435/4 |
| 2004/0223881 A1* | 11/2004 | Cunningham | G01N 21/45 422/82.05 |
| 2005/0014275 A1* | 1/2005 | Kitawaki | G01N 33/721 436/66 |
| 2005/0054082 A1* | 3/2005 | Pachl | G01N 21/27 435/287.2 |
| 2005/0079598 A1 | 4/2005 | Davis | |
| 2005/0148097 A1* | 7/2005 | Mizukami | G01N 33/5308 436/514 |
| 2005/0227374 A1* | 10/2005 | Cunningham | B01L 3/5085 436/518 |
| 2007/0138401 A1* | 6/2007 | Tokhtuev | G01J 3/0283 250/373 |
| 2007/0215809 A1* | 9/2007 | Mansfield | G01N 21/35 250/339.12 |
| 2008/0254440 A1* | 10/2008 | Uchida | C07K 16/10 435/5 |
| 2010/0075374 A1* | 3/2010 | Lim | C12P 21/02 435/68.1 |
| 2011/0025351 A1* | 2/2011 | van Breemen | C12Q 1/001 324/693 |
| 2015/0118675 A1* | 4/2015 | Ito | G01N 33/558 435/5 |
| 2015/0355156 A1* | 12/2015 | Boday | G01N 21/59 436/73 |
| 2016/0178491 A1* | 6/2016 | Civel | G01N 33/54393 435/30 |

FOREIGN PATENT DOCUMENTS

| | | | | |
|---|---|---|---|---|
| WO | 2004/005924 | | 1/2004 | |
| WO | WO 2004/005924 | * | 1/2004 | ........... G01N 33/543 |
| WO | 2004088319 | | 10/2004 | |

OTHER PUBLICATIONS

Label-Free Detection of Protein Interactions Using Deep UV Fluorescence Life-Time Micrscopy, Lee et al., Analytical Biochemistry, 367:104-110 (2007).

International Search Report and Written Opinion; PCT/US17/14732; dated Aug. 2, 2007.

* cited by examiner

*Primary Examiner* — Ann Y Lam
(74) *Attorney, Agent, or Firm* — Fish IP Law, LLP

(57) ABSTRACT

Devices, systems and methods for detecting molecules in a solid state using UV lights in a dry condition are provided. Interaction between a plurality of molecules, a conformational change of a molecule, a size difference between a plurality of molecules and a presence of a molecule can be detected in a dry environment by measuring a light absorption in at least one of light transmission mode and light reflection mode. In a preferred embodiment, the measurement of a light absorption is performed at a wavelength of ultraviolet light between 260 nm and 285 nm.

10 Claims, 3 Drawing Sheets

UV SOLID STATE DETECTION AND METHODS THEREFOR

This application is a national phase filing from PCT/US17/14732 filed Jan. 24, 2017, which claims priority to U.S. Provisional Patent Application No. 62/388,545, filed Feb. 1, 2016, each of which is incorporated by reference herein in its entirety.

FIELD OF THE INVENTION

The field of the invention is devices, systems and methods for detecting molecules in a solid state using ultra violet (UV) lights in a dry condition.

BACKGROUND

The background description includes information that may be useful in understanding the present inventive subject matter. It is not an admission that any of the information provided herein is prior art or relevant to the presently claimed invention, or that any publication specifically or implicitly referenced is prior art.

Molecule-molecule interactions, including protein-protein interactions and DNA-protein interactions occur in a wide range of biological phenomena, and many of them are often used for detecting and/or diagnosing a pathology and/or progress of a disease or symptoms. For example, detection of antigen-antibody interactions has been used to diagnose or determine a progress of infectious diseases or autoimmune diseases. Traditionally, molecule-molecule interactions are detected by labeling at least one of the molecules with a marker (e.g., fluorescence, biotin, organic dyes, enzyme conjugate, etc.). However, such labeling step takes extra cost and time such that it is very difficult to provide a user a detection results in a short time. Further, most of traditional methods require a liquid phase for signal detections, which often result in undesired nonspecific signals and/or bulk size of detection materials.

Some attempted to detect protein-protein interaction by detecting intrinsic fluorescence of a molecule without labeling the molecule. For example, Li et al., discloses a method of detecting antigen-antibody interactions using deep UV laser-based fluorescence lifetime microscopy. Here, a native fluorescence signal from intrinsic tryptophan emission was observed at 266 nm. However, in Li's method, native fluorescence signal is detected in a liquid phase. See Lee at al., Analytical Biochemistry 367 (2007) 104-110.

Some also attempted to detect conformational changes of a protein by attempt detecting intrinsic fluorescence of a molecule without labeling the molecule. For example, Lee at al. discloses microchip-based system for measuring concentrations and dynamic conformational changes in proteins without any use of extrinsic fluorescent labeling. Similar to Li et al., in Lee's method, difference of intrinsic fluorescence signal of tryptophan is detected to determine any conformational changes of a protein. However, this method is also limited to microfluidic system.

Others attempted to detect protein-protein interaction by detecting size differences before and after the interaction. For example, European Patent Application No. 1300684 to Price discloses detecting ligand-receptor binding by using colloidal magnetic particles. In this method, proteins bind to the colloidal magnetic particles, which increase overall size of the magnetic particle. Thus, the amount of analyte present in the solution can be determined by measuring the size of the magnetic particle associated with the analyte. Yet, this method is also limited to interaction and detection in a liquid phase.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Thus, there is still a need for improved devices, systems and methods for detecting molecules in a solid state using UV lights in a dry condition.

SUMMARY OF THE INVENTION

The inventive subject matter provides devices, systems and methods for detecting molecules in a solid state using UV lights in a dry condition.

One aspect of the invention includes a method for detecting a molecule-molecule interaction. In the method, a molecular interaction reaction between two molecules are detected without labeling two molecules in a dry environment by measuring light absorption in at least one of light transmission mode and light reflection mode. In a preferred embodiment, the light transmission and light reflection is measured at a wavelength in ultraviolet ranges.

Another aspect of the invention includes a method for detecting a conformational change of a molecule. In the method, a first value of the molecule in a first condition, and a second value of the molecule in a second condition are obtained in a dry environment. The first and second values are preferably obtained from a light absorption in at least one of light transmission mode and light reflection mode. Then, the first and second values are quantitatively compared to determine any conformational change of the molecule.

Still another aspect of the invention includes a method for detecting a difference between sizes of the first and second molecules. In the method, a first value of the first molecule and a second value of the second molecule are obtained in a dry environment. The first and second values are preferably obtained from a light absorption in at least one of light transmission mode and light reflection mode. Then, the first and second values are quantitatively compared to determine any size differences between the two molecules.

Still another aspect of the invention includes a method for quantitatively or qualitatively detecting a molecule. In the method, a signal of a molecule is measured on a support, without labeling the molecule, in a dry environment, using a light absorption in at least one of light transmission mode and light reflection. Then, using the signal against a background signal of the same support, the presence of the molecule is determined quantitatively or qualitatively.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
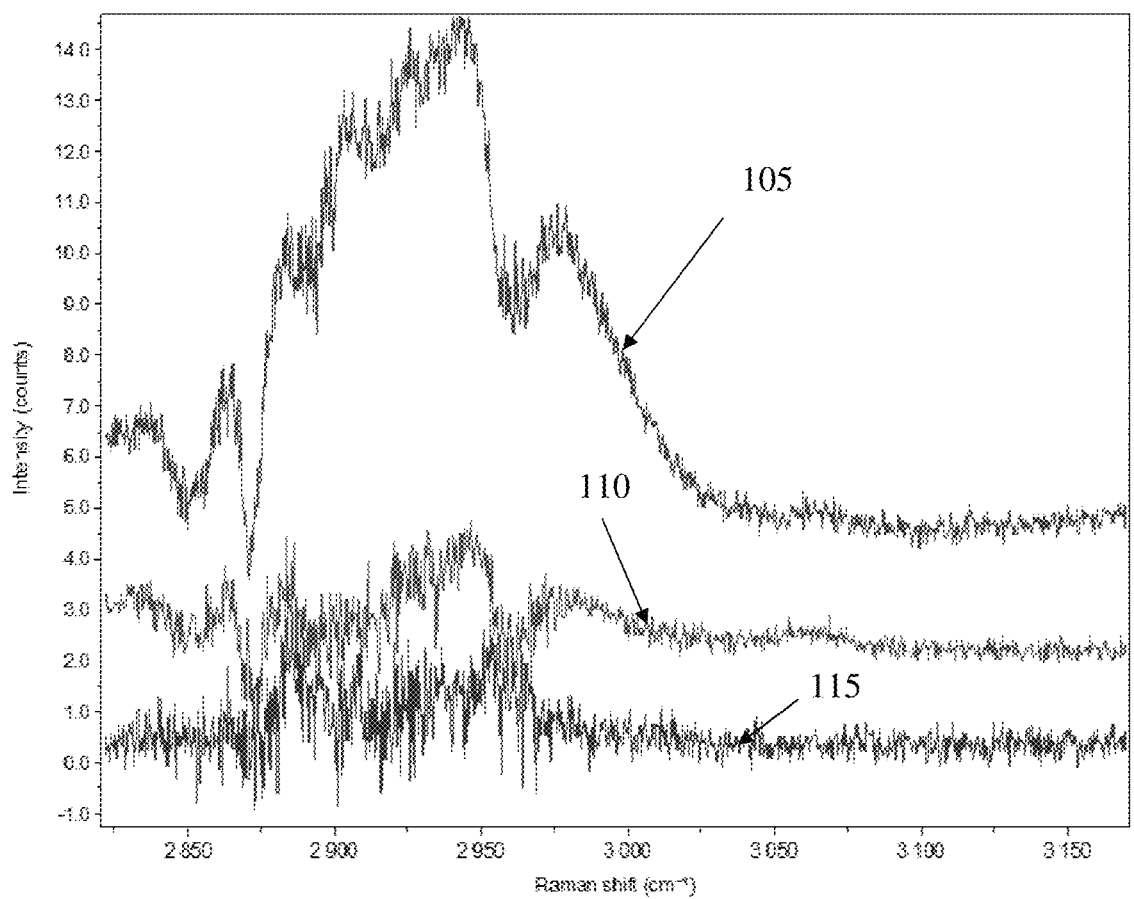
FIG. 1 is a graph showing differences in Raman Spectroscopy signal intensities among antigen only, antibody only, and antigen-antibody complex.

The inventors have discovered that biomolecules and their interactions, differences in their sizes and conformational changes can be effectively and sensitively detected by measuring UV light transmissions or reflections through or from the biomolecules on label-free biomolecules in a dry condition.

While the inventive subject matter is susceptible of various modification and alternative embodiments, certain illustrated embodiments thereof are shown in the drawings and will be described below in detail. It should be understood, however, that there is no intention to limit the invention to the specific form disclosed, but on the contrary, the invention is to cover all modifications, alternative embodiments, and equivalents falling within the scope of the claims.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

In some embodiments, the numbers expressing quantities or ranges, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements. Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified, thus fulfilling the written description of all Markush groups used in the appended claims.

In one especially preferred aspect, the inventors therefore contemplate a method of detecting molecule-molecule interactions between a plurality of molecules. In this contemplated method, molecule-molecule interactions between the plurality of molecules can be detected without labeling (e.g., fluorescence, biotin, organic dyes, enzyme conjugate, etc) by measuring a light absorption to the plurality of molecules. Most preferably, the light absorption is measured in either light transmission mode or light reflection mode, or both.

As used herein, a molecule is any type of molecule which absorbs light at a wavelength in UV range. Preferably, the molecule includes proteins (e.g., a membrane protein, an antigen, an antibody (e.g., IgA, IgE, IgM, IgG, IgD), a secretive protein, a DNA-binding protein, a RNA-binding protein, enzymes, a structural protein, a signaling protein, a transport protein, a regulatory protein, a sensory protein, a motor protein, a receptor protein, a ligand protein, a storage protein, a hormone, etc.). The proteins include a naïve protein, a denatured protein (e.g., by temperature, by pH, etc.), or a protein with one or more post-translational modifications (e.g., glycosylation, phosphorylation, acetylation, amidation, hydroxylation, sulfation, ubiquitylation, etc.).

The molecule also includes peptides (e.g., fragments of a protein such as a carboxyl terminus of the protein, an epitope of an antigen, neuropeptide, amyloid peptide, etc.). The peptides can be a naturally generated peptide or an artificially generated peptide (e.g., by subcloning and purification, etc.). Any size of peptide that is long enough to absorb UV light can be used. For example, the peptide can be between 4-600 amino acids, preferably between 10-500 amino acids, more preferably between 20-400 amino acids, most preferably between 50-300 amino acids.

In some embodiments, the molecule includes nucleotides. As used herein, nucleotide includes deoxyribonucleic acid (DNA, double stranded, single stranded), phosphothioate, ribonucleic acid (RNA, including tRNA, mRNA, rRNA), microRNA (miRNA), small hairpin RNA (shRNA), small interfering RNA (siRNA), small nuclear RNA (snRNA), antisense RNA, and so on.

In some embodiment, the molecule is a combination of nucleotide and proteins. For example, the molecule can be a chromosome fragment, in which DNA molecule is associated with chromosomal proteins.

When a molecule interacts with another molecule, the molecule-molecule complex generally has different size from either of the molecules. For example, when an antigen and antibody interact with each other and form an antigen-antibody complex, such complex generally has a larger size (e.g., a larger diameter of the complex, a greater overall volume of the complex, a higher molecular weights, etc.) than antigen alone or an antibody alone. Under Beer-Lambert law, the amount of light transmitted through a molecule (or groups of molecules) diminishes exponentially as it travels through the molecule. It is directly proportional to the thickness of the molecule (or groups of molecules) and to the concentration of the molecule (or groups of molecules) in a sample. The inventors found that when two molecules interacts to form a molecule-molecule complex, such complex generally absorb more lights than a single molecule alone. For example, an antigen-antibody complex absorbs more lights than antigen alone or an antibody alone, as shown in example below.

It is preferred that the difference in molecular weights between the molecule complex (e.g., antigen-antibody complex, ligand-receptor complex, etc) and a single molecule (e.g., ligand, receptor, antigen, antibody, etc.) is at least 10 kda, preferably at least 20 Kda, more preferably at least 50 Kda.

In a preferred embodiment, the absorption of light can be measured either light transmission mode or light reflection mode, or both. A transmission spectrum will have its maximum intensities at wavelengths where the absorption is weakest because more light is transmitted through the sample. Thus, the light transmission through the antigen-antibody complex is less than those through either antigen or antibody alone. Conversely, the reflection will have its maximum intensities at wavelengths where the absorption is weakest because more light is reflected through the sample. Thus, the light reflection from the antigen-antibody complex is greater than those through either antigen or antibody alone.

In a preferred embodiment, the measurement of the light absorption in either light transmission mode or light reflection mode is performed at one or more wavelength in UV range (between 10 nm and 400 nm), preferably between 150 nm and 350 nm, more preferably between 240 nm and 300 nm, most preferably between 250 nm and 290 nm. In this embodiment, the wavelength in UV range is selected to avoid any signal contamination from auto fluorescence of the biomolecules (e.g., from tryptophanes and other amino acids with aromatic ring(s) of a protein, etc.).

In some embodiments, measurement of the light absorption can be performed using an optical assembly, preferably using a magnifying optical assembly (e.g., microspectroscopy, etc.), which comprises a light source and light detector. Any suitable source of lights is contemplated. A preferred source of lights includes UV light emitting diodes (UV LED), which emits UV lights with wavelengths between 240 nm and 355 nm, and a UV laser with a center wavelength between 250 nm and 290 nm. In a preferred embodiment, the bandwidth of the UV lights is maintained in a narrower range in order to prevent detecting excess and nonspecific scattered lights. In this embodiment, it is preferred that the UV light source is a monochromatic UV lights that emits UV lights with a bandwidth of the UV lights is less than 50 nm, preferably less than 30 nm, more preferably less than 20 nm.

In a preferred embodiment, at least one molecule that can make a molecule-molecule complex (e.g., antigen of antigen-antibody complex, or antibody of antigen-antibody complex) is immobilized on a support. Any suitable support for molecular absorption and signal detection by a light detector is contemplated. In some embodiments, the support is a solid support, which includes wells of a multiwall plate (e.g., a plastic polymer plate, a glass plate, etc), a bead (e.g., color-coded or magnetic), a silica, an acrylic resin. In other embodiments, the support is a flexible support including an adsorptive film (e.g., nitrocellulose or micro/nanoporous polymeric film), a fibrous support (e.g., a paper, etc), a light-reflective support (e.g., light-reflective microporous sheet, etc.), or a translucent or transparent support. Preferably, the molecules are immobilized on a support as an array (e.g., in a predetermined distances and diameter) so that automatic reading and analysis of the light absorptions are readily available.

The molecule is immobilized on a support by any suitable mechanisms. For example, it is contemplated that the molecule is immobilized on a support by covalent binding, UV crosslinking, adsorption, fixing via an intermediary binding molecule (e.g., a linker, etc.) to the support. Based on a size of area where the molecule is immobilized (reactive surface area (e.g., a well of a multiwall plate, a distinct surface area where the molecule is immobilized, etc.)), the quantity of molecules immobilized on the support can vary. In some embodiments, the reactive surface area can range between 10 $cm^2$ and 10 $mm^2$, between 10 $mm^2$ and 1 $mm^2$, between 1 $mm^2$ and 0.1 $mm^2$. In those embodiments, the quantity of molecules immobilized per a reactive surface can be between 1 mg and 100 mcg, 100 mcg and 10 mcg, between 10 mcg and 1 mcg, between 1 mcg and 100 ng, between 10 ng and 1 ng.

In order to obtain light transmission and/or reflection signals with minimum artifacts, the inventors contemplate that the reactive surface area of the surface maintains homogeneity (e.g., substantially uniform) in thickness, roughness, particle distribution, or polymerization status. For example, it is preferred that each reactive surface area has uniform molar attenuation coefficient within the reactive surface area, and has substantially identical (e.g., less than 5% variance, preferably less than 3% variance, more preferably less than 1% variance) to molar attenuation coefficient of other reactive surface area on a same or same type of support.

In an especially preferred embodiment, the detection of light absorption is performed in a dry environment. As used herein, the dry environment is a condition with residual solvent content (e.g., water, phosphate buffered saline, etc.) less than 1 mg, preferably less than 0.5 mg, more preferably less than 0.2 mg of solvent per 1 $mm^2$ of support at a location where the molecule is immobilized (e.g., surface of well of an microwell plate, etc).

Any suitable methods to obtain dry conditions are contemplated. For example, desired dry condition can be obtained by evaporating solvents (e.g., air dry, etc.), evaporating solvents by heating, infrared radiation, vacuum dry, solvent exchange, removing excessive solvent by blotting (e.g., with filter paper, etc.), or spinning (e.g., centrifugation). In some embodiments, where maintenance of structure of molecule is desired, the dry condition can be obtained while molecules are at least partially protected (e.g., covered, coated, etc.) by humectants (e.g., propylene glycol, lithium chloride, etc.).

The molar attenuation coefficient, which is an intrinsic property of a molecule, is a measurement of how strongly a chemical species attenuates light at a given wavelength. The molar attenuation coefficient changes with a conformational change of a molecule. Thus, another aspect of the inventive subject matter is detecting a conformational change of a molecule by detecting a light absorption in at least one of light transmission mode and light reflection mode of the molecule in two different conditions, in a dry environment.

It is contemplated that many molecules undergo conformational changes that renders light transmission or light reflection signals different from naïve protein (before conformational changes). Thus, a first value of light transmission or light reflection signal of a molecule can be obtained in a first condition, and a second value of light transmission or light reflection signal of the molecule can be obtained in a second condition. Then, the first and second values are quantitatively compared to determine whether the molecule has undergone conformational change in the second condition compared to the first condition, or vice versa.

Many conditions are contemplated to induce conformational change of a molecule. For example, if a molecule is a protein, a first condition can be a reduced state with a disulfide bond and a second condition can be an oxidized state with two thiol groups. For another example, a first condition can be native protein without a post translational modifications and a second condition can be a post-translationally modified state. For still another example, the first condition is a folded state (into tertiary or quaternary), and the second condition is an unfolded state. For still another example, the first condition is a binding state with another molecule, and the second condition is a nonbinding state.

It is expected that the molar attenuation coefficient is different between two or more molecules having different sizes (e.g., molecular weight, volume, diameter, etc.). Thus, another aspect of the inventive subject matter is detecting a difference between sizes of two molecules by detecting a light absorption in at least one of light transmission mode and light reflection mode of the two molecules in a dry environment.

In a preferred embodiment, molar attenuation coefficient of at least one of two or more molecules are pre-determined so that the relative size difference of other molecules can be readily determined based on the pre-determined molar attenuation coefficient of the molecule and the molecule's light transmission or light reflection signal value. It is further contemplated that molar attenuation coefficients of several molecules in a same species (e.g., proteins as one species, peptides as one species, nucleotides as one species, etc) can be measured to predetermine the relationship between the molar attenuation coefficients and size of the molecules (e.g., linear relationship, exponential relationship, etc.). In this embodiment, approximate size of a new molecule can be readily determined by measuring light transmission or light reflection signal value and compare in the predetermined relationship between the molar attenuation coefficients and size of the molecules.

In some embodiments, in order to render distinct and meaningful differences in light transmission or light reflection signal value related to molecular size differences, it is preferred that the differences in molecular weights (of proteins or peptides) between or among a plurality of molecules are at least 10 kda, preferably more than 20 kda, more preferably more than 30 kda. In case the molecules are nucleotides, it is preferred that the size difference between or among a plurality of molecules are at least 10 base pairs (bp), preferably more than 50 bp, more preferably more than 100 bp.

As the molecular attenuation coefficient is an intrinsic property of a material or a molecule, it is expected that the molecular attenuation coefficient of a support and the molecular attenuation coefficient of a molecule (especially biomolecules) would be sufficiently different to be detected with light transmission or light reflection. Thus, another aspect of the inventive subject matter includes quantitatively or qualitatively detecting a molecule without labeling the molecule, using light absorption in at least one of light transmission mode and light reflection to obtain light transmission or light reflection signal of the molecule, in a dry environment. Preferably, the molecule is placed (e.g., immobilized, dried on, etc.) on a support, which is suitable for measuring a light transmission or light reflection signal of the molecule. The light transmission or light reflection signal of the support are measured separately to confirm a background signal. It is contemplated that light transmission or light reflection signal of a support having biomolecules placed thereon would be different from light transmission or light reflection signal of support alone. Thus, by comparing the light transmission or light reflection signal of a support only and with samples (e.g., biomolecules), a presence of biomolecules on a support can be determined without labeling the biomolecules.

Example I: Raman Spectroscopy

FIG. 1 shows an exemplary data of detecting molecule-molecule interactions using Raman spectroscopy in a dry condition. In this example, *Helicobacter pylori* (*H. pylori*) antigens are immobilized in the first reactive surface of a multiwell plate. In the second reactive surface, the *H. pylori* antigens are immobilized in, and primary antibodies against the antigens in a phosphate buffer are added over the immobilized antigens so that primary antibodies can interact with antigens. In a third reactive surface, the *H. pylori* antigens are immobilized and antibodies in a phosphate buffer are added over the immobilized antigens so that antibodies can interact with antigens. Then, secondary antibodies (or conjugate) against the primary antibodies are added over the immobilized antigen-antibody complex to form antigen-primary antibody-secondary antibody complex. The excessive buffer is removed and the surface was dried (e.g., air dried, centrifuged, desiccated, etc.). Signal intensities (shown in an arbitrary unit) of antigen alone 115, antigen-antibody complex 110 and antigen-primary antibody-secondary antibody complex 105 are measured at 532 nm wavelength. As shown in FIG. 1, antigen-antibody complex shows generally higher signal intensity in all Raman shifts. Most notably, the signal increase was most significant and distinct with antigen-primary antibody-secondary antibody complex, which implicates that by adding secondary antibody, it could boost the signal with Raman spectroscopy.

While the experiment shown in FIG. 1 used 532 nm wavelength for measuring signals of molecule complex, it is contemplated that other wavelengths can be used. For example, a wavelength at 785 nm, 1064 nm, near infrared are contemplated to produce similar results. Further, a Laser-induced breakdown spectroscopy (LIBS), which is a type of atomic emission spectroscopy that uses a highly energetic laser pulse as the excitation source, is also contemplated for such experiments.

While Raman spectroscopy provides a meaningful data at a very small area (0.5 micron of microscope field), its use can be limited due to (1) use of a very limited section of the spectra and (2) complicated and large size instruments.

Example II: UV Microspectroscopy

Figure 2:
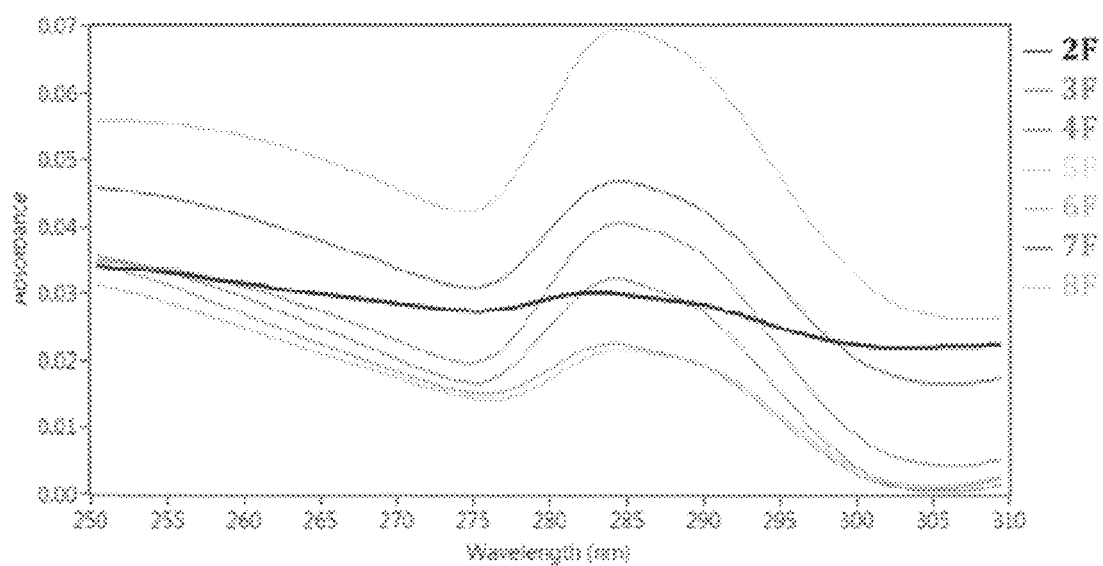
FIG. 2 illustrates a graph showing differences in UV Spectroscopy signal intensities among antigen only, antibody only, and antigen-antibody complex.

FIG. 2 shows an exemplary data of detecting molecule-molecule interaction using UV microspectroscopy in a dry condition. In this example, inventors could distinguish molecules based on their sizes, and the total energy that they absorb or release. In this example, signals are detected at a 285 nm wavelength in a relatively larger detection area (about 200 uM).

In general, protein samples for UV microspectroscopy are prepared as follows. First, a solid surface is activated to form reactive surfaces. Then, antigens (or antibodies in some instances) are immobilized (e.g., attached, etc.) on the reactive surface. Then, the reactive surfaces with antigens are treated with blocking solutions to block non-specific binding sites. Then, positive or negative samples (e.g., human sera positive to the infection (of antigen) that contains primary antibodies against the antigens, or human sera negative or free from infection (of antigen), etc.) are placed on the reactive surface. In some embodiments, secondary antibodies or conjugates configured to bind the primary antibodies are added to the reactive surface in order to form an antigen-primary antibody-secondary antibodies (or conjugate) complex.

In this example, *H. pylori* antigens are immobilized in the first reactive surface (2 F) of a multiwell plate (2 F). In the second reactive surface (3 F), the *H. pylori* antigens are immobilized in, and primary antibodies positive against the antigens are added over the immobilized antigens so that primary antibodies can interact with the antigens. In a third reactive surface (4 F), the *H. pylori* antigens are immobilized in, and negative antibodies (supposedly nonreactive to the antigens) are added over the immobilized antigens. In a fourth reactive surface (5 F), the *H. pylori* antigens are immobilized in, and primary antibodies positive against the antigens are added over the immobilized antigens so that primary antibodies can interact with antigens. In a fifth reactive surface (6 F), the *H. pylori* antigens are immobilized in, and negative sera (supposedly not reactive to the antigens) are added over the immobilized antigens. For the fourth and fifth reactive surfaces, conjugates (or can be substituted with secondary antibodies) are added. Also, in the experiment presented in FIG. 2, the effects of blocking solutions (modified formula of bovine serum albumin (BSA) solutions in a buffer) in blocking non-specific binding are tested and shown in (7 F) and (8 F).

In this example, the light absorbance of each reactive surface is measured at a wavelength of 285 nm. As shown in FIG. 2, absorbance of UV light is greater with addition of sera interacting with the antigen (compare 2 F with 3 F and 4 F). Thus, this data indicates that UV spectroscopy can be used to measure or determine molecule-molecule (antigen-antibody in this experiment) interactions without labeling molecules.

Figure 3A:
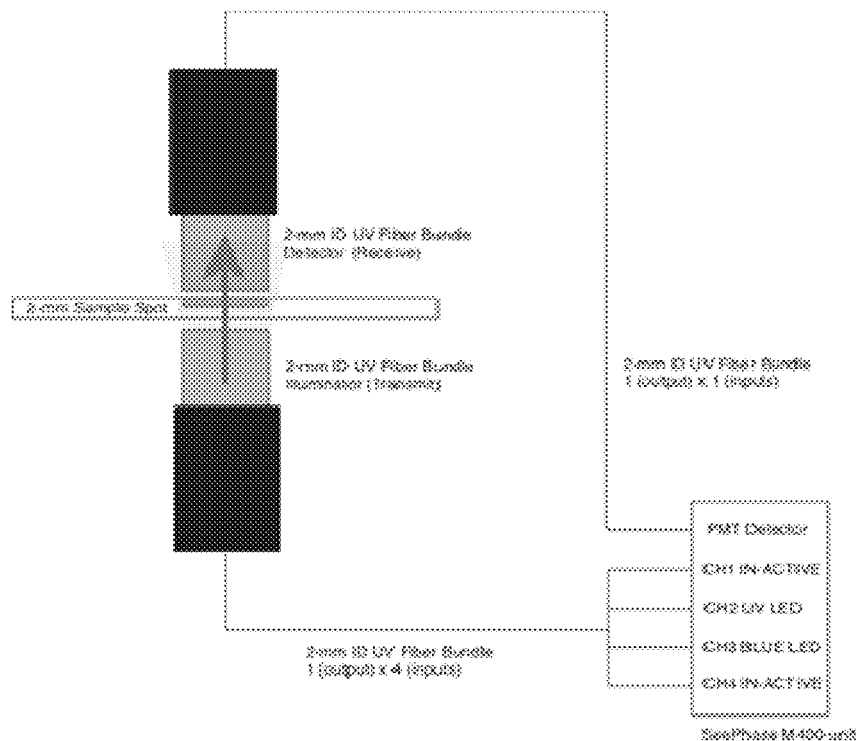
FIG. 3A illustrates a schematic diagram of a UV detection system using light transmission.
Figure 3B:
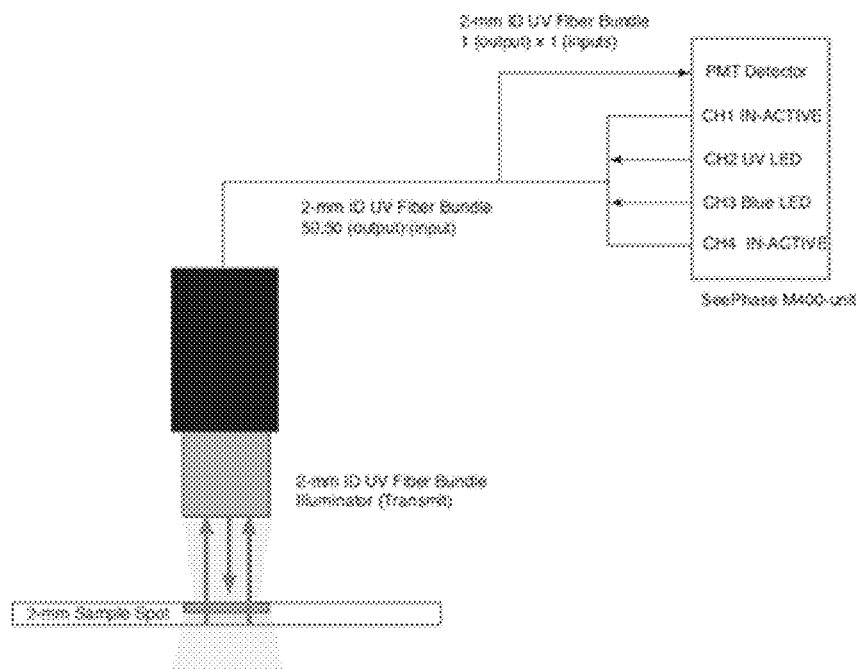
FIG. 3B illustrates a schematic diagram of a UV detection system using light reflection.

FIGS. 3A and 3B illustrate fiber optic multi-channel detection system that detects light transmission (FIG. 3A) through the sample or light reflection (FIG. 3B) from the sample in two different modes. In an exemplary embodiment, the optical assembly includes a fiber optic multi-channel detection system that monitors and tracks changes in optical transmission or reflection through a medium when using a frequency modulated UV LED and a high sensitivity UV detector. It is contemplated that this system, uses a narrow bandwidth, high optical power, UV LED with peak emission intensity centered at 280-nm, and a high sensitivity photodetector (photomultiplier tube PMT) equipped with a band pass optical filter centered at 280-nm with a pass bandwidth of ±30 nm from the center wavelength. This system can be integrated to an instrument (e.g., a microscope) to monitor the light intensity activity of UV absorbing biomolecules immobilized on the surface of conventional microtiter plate test wells (or other suitable solid phases) to monitor the UV absorption activity.

In an especially preferred embodiment, this system uses a fiber optic probe consisting of a 2-mm diameter tube integrating a dense array of 100-micron diameter fibers, for use in transmission and reflection light intensity monitoring. In the transmission mode, one fiber is connected to one of the UV LEDs light engines of the detections system, and connected at the bottom entry point of the instrument (e.g., a microscope). A second fiber is used to collect the light transmitted through the microtiter plate wells and to direct the light to the high sensitivity photodetector receiver (PMT) of this system to monitor the changes in the light transmission. In the reflection mode, a 1×2 bifurcated fiber, also consisting of a 2-mm diameter tube integrating a dense array of 100-micron diameter fibers, is connected to the top port of the instrument (such as a microscope used in our preliminary studies for showing the feasibility) by using the one arm of the 1×2 splitter. The other two arms at the other end of the splitter are connected to the LED light engine and to the PMT photodetector, in this manner, the light reflected from the bottom surface of the microtiter plate can be measure by launching light in the fiber connected to the UV LED, and to monitor the reflected light intensity from the plate microtiter using the fiber connected to the PMT photodetector.

It is contemplated that light absorption detection method in dry condition using fiber optic multi-channel detection system can be utilized in many different purposes. For example, the method can be used to detect the amount or presence of molecules in the sample without labeling the molecules. In the light transmission mode, it is contemplated that more and larger particles at the sample would absorb more light and render less light transmission through the sample. In the light reflection mode, it is contemplated that more and larger particles at the sample would absorb more light and render less light transmission through the sample, and further absorb more light that is transmitted through the sample and reflected from the bottom of the support toward the sample. Thus, the amount of the reflected lights would be decreased further with more and larger particles at the sample.

Table 1 shows one exemplary data showing that light transmission and reflection (double transmission) decreases as the molecule concentration increases. In this experiment, bovine serum albumin (BSA) is immobilized in two different types of support: translucent tape (CT) and a nitrocellulose film (Nit). On both types of support, the amount of light transmission through immobilized BSA is lowest when the BSA concentration is highest (20%) among samples. Similarly, the amount of light reflection through immobilized BSA is lowest when the BSA concentration is highest (20%) among samples. Consequently, the amount of light transmission and reflection through immobilized BSA is highest when the BSA concentration is lowest (2.5% or 0.312% or 0.019%) among samples.

TABLE 1

| BSA Conc. | CT-Transmission | Nit-Reflection | CT-Reflection | CT-Transmission |
|---|---|---|---|---|
| 20% | 0.04 | 0.47 | 0.41 | 0.26 |
| 10% | 0.04 | 0.49 | 0.42 | 0.30 |
| 5% | 0.13 | 0.50 | 0.43 | 0.32 |
| 2.5% | 0.16 | 0.50 | 0.47 | 0.34 |
| 1.25% | | 0.52 | 0.50 | 0.36 |
| 0.625% | | 0.53 | 0.51 | 0.41 |
| 0.312% | | 0.53 | 0.54 | 0.42 |
| 0.156 | | | 0.57 | 0.45 |

TABLE 1-continued

| BSA Conc. | CT-Transmission | Nit-Reflection | CT-Reflection | CT-Transmission |
|---|---|---|---|---|
| 0.078 | | | 0.58 | 0.49 |
| 0.039 | | | 0.60 | 0.51 |
| 0.019 | | | 0.62 | 0.55 |

For another example, such method can be used to determine antigen-antibody interactions in both light transmission mode and light reflection mode (double transmission mode). Table 2 shows exemplary experiment data that light transmission and reflection (double transmission) decreases as antigen interacts with antibody to form antigen-antibody complex. In this experiment, three types of supports were used to immobilize *H. pylori* antigens that can be found in human sera: a translucent tape (CT), an opaque tape (DT), and a nitrocellulose film (Nit). Antibodies to these antigens can be found in human sera in patients with specific gastrointestinal disorders such as ulcer. In the experiment using a translucent tape (CT) as a support, light transmission decreased when the antigens interact with positive control (a human serum positive with *H. pylori* infection) and human a-*H. pylori* antibodies (from 0.42 to 0.31 with positive control, and to 0.11 when second antibody is added in the first experiment, and from 0.53 to 0.35 with positive control, and to 0.32 when the second antibody is added in the second experiment (all data are represented in relative values).

In addition, in the experiment using translucent tape (CT), an opaque tape (DT), and a nitrocellulose film (Nit), in the light reflection mode, light reflection was decreased with positive control (Pos.) (from 0.42 to 0.39 on translucent tape, from 0.42 to 0.39 on opaque tape, and 0.51 to 0.47 on nitrocellulose film) and further with second antibodies (from 0.39 to 0.36 on translucent tape, from 0.39 to 0.37 on opaque tape).

TABLE 2

| Solid phase | CT-Reflection | CT-Transmission | DT-Reflection | CT-Transmission | Nit-Reflection |
|---|---|---|---|---|---|
| Blank | | | | | 0.52 |
| Ag | 0.42 | 0.42 | 0.42 | 0.53 | 0.51 |
| Ag + Pos | 0.39 | 0.31 | 0.39 | 0.35 | 0.47 |
| Ag + Neg | | | | | 0.49 |
| Ag + Pos + Ab | 0.36 | 0.11 | 0.37 | 0.32 | |

Table 3 shows another exemplary experiment data that light transmission and reflection decreases as antigen interacts with antibodies to form antigen-antibody complex, on epoxy support. Inventors found that both light transmission and light reflection increase where antigens on the epoxy support are placed at lower concentrations (1/2 diluted and 1/4 diluted compared to undiluted (all data are represented in relative values). Also, both light transmission and reflections decrease when antigen interacts with positive control (a human serum positive with *H. pylori* infection) and/or conjugate. However, when the positive control is diluted to 1/4 concentration, both light transmission and reflection in antigen with diluted positive control show no significant difference from antigen alone, indicating that antigen-positive control complex made in the sample with 1/4 concentration of positive control could not reach the threshold (the concentration is close enough to generate a signal similar to that of a negative sample) for a detection with a meaningful significance.

TABLE 3

| Solid phase | Epoxy Transmission | Epoxy Reflection | Epoxy Transmission | Epoxy Reflection |
|---|---|---|---|---|
| Ag | 0.19 | 0.40 | 0.49 | 0.48 |
| Ag ½ diluted | 0.25 | 0.41 | | |
| Ag ¼ diluted | 0.40 | 0.44 | | |
| Ag + positive 1 | | | 0.45 | 0.46 |
| Ag + pos.1 + conj | | | 0.42 | 0.45 |
| Ag + ½ pos. | | | 0.45 | 0.47 |
| Ag + ½ Pos. + conj | | | 0.39 | 0.45 |
| Ag + ¼ Pos. | | | 0.50 | 0.49 |
| Ag + ¼ Pos. + conj. | | | 0.47 | 0.47 |

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method for detecting a molecule-molecule interaction, comprising:
   detecting a molecular interaction reaction between a first molecule and a second molecule, without labeling first and second molecules, in a dry environment, by measuring light absorption in at least one of light transmission mode and light reflection mode, wherein the dry environment comprises a test surface selected from the group consisting of a plate, a bead, a film, and a porous membrane.

2. The method of claim 1, wherein the first molecule is fixed on a support.

3. The method of claim 1, wherein the first molecule is placed in a form of an array.

4. The method of claim 1, wherein at least one of the light transmission and light reflection modes is measured at a wavelength in ultraviolet ranges.

5. The method of claim 1, wherein the first molecule is a protein or a peptide.

6. The method of claim 1, wherein the first molecule is an antigen, and the second molecule is an antibody, or wherein the first molecule is an antibody, and the second molecule is an antigen.

7. The method of claim 1, wherein a molecular weight difference between the first molecule and a complex comprising the first and second molecules is at least 20 kDa.

8. The method of claim 1, wherein at least one of the first and second molecules is a nucleic acid.

9. The method of claim 1, wherein the dry environment comprises a condition with residual solvent content less than 1 mg of solvent per 1 $mm^2$ of support at a location where the first and/or second molecule is placed.

10. The method of claim 1, wherein measuring is performed using at least one of a magnifying optical assembly, Raman spectroscopy, and UV microspectroscopy.

* * * * *